(12) United States Patent
Robinson

(10) Patent No.: US 9,839,527 B2
(45) Date of Patent: Dec. 12, 2017

(54) EXPANDABLE INTER-BODY FUSION DEVICES AND METHODS

(71) Applicant: James C. Robinson, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 0 days.

(21) Appl. No.: 14/062,799

(22) Filed: Oct. 24, 2013

(65) Prior Publication Data

US 2014/0114420 A1    Apr. 24, 2014

Related U.S. Application Data

(60) Provisional application No. 61/717,770, filed on Oct. 24, 2012, provisional application No. 61/794,668, filed on Mar. 15, 2013.

(51) Int. Cl.
*A61F 2/44* (2006.01)
*A61F 2/28* (2006.01)
*A61F 2/30* (2006.01)

(52) U.S. Cl.
CPC ...... *A61F 2/447* (2013.01); *A61F 2002/2817* (2013.01); *A61F 2002/2835* (2013.01); *A61F 2002/3081* (2013.01); *A61F 2002/30482* (2013.01); *A61F 2002/30484* (2013.01); *A61F 2002/30502* (2013.01); *A61F 2002/30504* (2013.01); *A61F 2002/30538* (2013.01); *A61F 2002/30556* (2013.01); *A61F 2002/30579* (2013.01); *A61F 2002/30629* (2013.01); *A61F 2002/30779* (2013.01); *A61F 2002/30784* (2013.01); *A61F 2002/30787* (2013.01); *A61F 2002/30828* (2013.01); *A61F 2002/4475* (2013.01)

(58) Field of Classification Search
CPC ............ A61F 2/4455; A61F 2002/4475; A61F 2002/30471; A61F 2002/4628; A61F 2002/443; A61F 2/44–2/447
USPC ............................................. 623/17.11–17.16
See application file for complete search history.

(56) References Cited

U.S. PATENT DOCUMENTS

| | | | | | |
|---|---|---|---|---|---|
| 4,759,769 | A | * | 7/1988 | Hedman et al. | 623/17.13 |
| D392,387 | S | * | 3/1998 | Michelson | D24/155 |
| 6,102,950 | A | * | 8/2000 | Vaccaro | 623/17.16 |
| 6,190,414 | B1 | * | 2/2001 | Young et al. | 623/17.15 |
| 6,193,757 | B1 | * | 2/2001 | Foley et al. | 623/17.16 |
| 6,368,351 | B1 | * | 4/2002 | Glenn | A61F 2/4455 606/247 |
| 6,419,705 | B1 | * | 7/2002 | Erickson | 623/17.16 |

(Continued)

FOREIGN PATENT DOCUMENTS

WO    WO 2011007240 A1    1/2011

*Primary Examiner* — Jan Chistopher Merene
*Assistant Examiner* — Steven Cotroneo
(74) *Attorney, Agent, or Firm* — FisherBroyles, LLP; Anthony J. DoVale

(57) ABSTRACT

An expandable inter-body fusion device is presented. The expandable inter-body fusion device has a first plate and a second plate that can be manipulated to change the height and angle of lordosis. Also presented is a method of using an expandable inter-body fusion device in an inter-body fusion procedure, and a method of using an expandable trial to size the correct expandable inter-body fusion device for use in the aforementioned procedure.

24 Claims, 16 Drawing Sheets

(56) References Cited

U.S. PATENT DOCUMENTS

| | | | |
|---|---|---|---|
| 6,454,807 B1* | 9/2002 | Jackson | A61F 2/447 |
| | | | 623/17.15 |
| 6,652,584 B2* | 11/2003 | Michelson | 623/17.11 |
| 6,716,247 B2* | 4/2004 | Michelson | 623/17.16 |
| 6,808,537 B2* | 10/2004 | Michelson | A61F 2/4455 |
| | | | 623/17.15 |
| 7,655,027 B2* | 2/2010 | Michelson | 606/279 |
| 7,887,588 B2* | 2/2011 | Rapp | 623/17.11 |
| 7,892,286 B2* | 2/2011 | Michelson | 623/17.15 |
| 8,092,534 B2* | 1/2012 | Eckhardt | 623/17.11 |
| 8,105,382 B2* | 1/2012 | Olmos | A61F 2/447 |
| | | | 623/17.15 |
| 8,221,502 B2* | 7/2012 | Branch, Jr. | 623/17.15 |
| 8,496,706 B2* | 7/2013 | Ragab et al. | 623/17.11 |
| 9,445,919 B2* | 9/2016 | Palmatier | A61F 2/447 |
| 2002/0138146 A1* | 9/2002 | Jackson | 623/17.15 |

\* cited by examiner

EXPANDABLE INTER-BODY FUSION DEVICES AND METHODS

CROSS REFERENCE TO RELATED APPLICATIONS

This application claims the benefit of and priority to U.S. Provisional Patent 61/717,770, filed Oct. 24, 2012, and U.S. Provisional Patent 61/794,668, filed Mar. 15, 2013, both of which are incorporated in their entirety in this document by reference.

FIELD OF THE INVENTION

This invention relates generally to spinal surgery, and more particularly to devices and methods for stabilization of the spine in association with placement of an expandable inter-body construct for inter-body fusion or the like.

BACKGROUND OF THE INVENTION

Damage or disease that affects the integral structure of a bone structure or more specifically, a vertebral body within an individual's spinal column may lead to neurologic impairment with possible permanent damage to the surrounding tissue. Maintaining proper anatomic spacing within a bone structure and the spinal column is critical to ensuring continued functionality of the surrounding tissue and for the spinal column, the spinal cord and nerve roots and therefore, avoidance of long term serious neurological impairment.

Typically, spinal implants that are used as a spacer type of device have a fixed overall length and are implanted without the ability to adjust the degree of expansion or curvature without using multiple insertion instrumentation. Some of the known procedures for introducing spinal implants comprise Anterior Lumbar Inter-body Fusion ("ALIF"), Lateral Lumbar Inter-body Fusion ("LLIF"), Posterior Lumbar Inter-body Fusion ("PLIF"), Oblique Lumbar Inter-body Fusion ("OLIF"), and the like. A need remains for a multi-purpose instrument to be used to implant a spacer type of implant that allows the surgeon to minimize the size of the surgical incision, facilitate the operative technique and decrease patient morbidity.

SUMMARY

Presented herein is an expandable inter-body fusion device that comprises a first plate and a second plate. The first plate has an upper bone contact surface and the second plate has a lower bone contact surface. In one aspect, the two plates are connected hingedly in a manner to permit changing the angular relationship between the upper contact surface and the lower contact surface. In another aspect, the two plates are connected to permit translation of the pivot point vertically to enable changing of the spatial relationship of the first plate relative to the second plate. As a result, the volume of the cavity will necessarily be variable.

In an exemplified aspect, at least one of the first plate and the second plate define at least one graft window that is in communication with the interior cavity. In another aspect, the upper contact surface of the first plate comprises ridges for frictionally engaging the first vertebra. As can be appreciated, the lower contact surface of the second plate can also comprise ridges to frictionally engage the second vertebra. In yet another aspect, the first plate and the second plate define at least one graft window. The at least one graft window defined in the first plate can also be at least partially overlying the at least one graft window of the second plate, thereby permitting bone growth therethrough.

In another aspect, the inter-body fusion device further comprises an insert configured for insertion between the first and second plates and substantially into the interior cavity. The insert has a top face and a bottom face, where the top face engages at least a portion of the first plate and the bottom face engages at least a portion of the second plate. Depending upon the thickness of the insert and the angle of the top face relative to the bottom face, the insert is configured to move either the first or second plate, or both, to substantially set the distance and angle of the upper contact surface relative to the lower contact surface.

The expandable inter-body fusion device can also further comprise an end cap configured to engage at least a portion of the first plate and positioned thereon the trailing end of the inter-body fusion device, thereby helping to retain the insert therein the interior cavity. In one aspect, the cap is shaped to conform to the trailing end of the inter-body fusion cage and be sized to cover and enclose the interior cavity such that the bone fusion material is retained therein. As such, the size of the end cap can be chosen after insertion of the desired insert, so that the height of the inter-body fusion device is known.

Related methods of operation are also provided. Other apparatuses, methods, systems, features, and advantages of the expandable inter-body fusion device and the method of its use will be or become apparent to one with skill in the art upon examination of the following figures and detailed description. It is intended that all such additional apparatuses, methods, systems, features, and advantages be included within this description, be within the scope of the expandable inter-body fusion device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention Like reference characters used therein indicate like parts throughout the several drawings.

DESCRIPTION OF THE INVENTION

Figure 1:
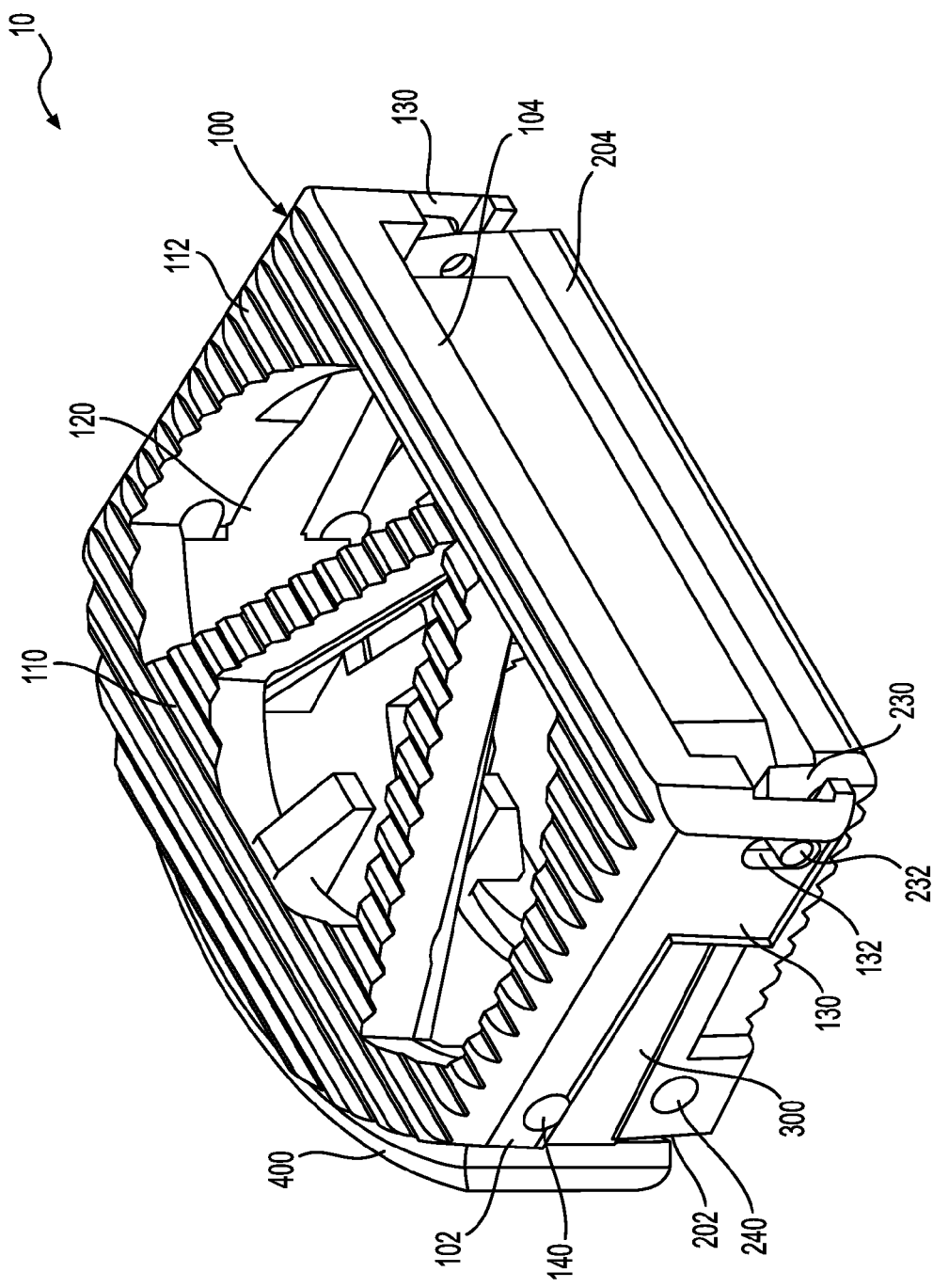
FIG. 1 is a perspective view of one aspect of an expandable inter-body fusion device.
Figure 2:
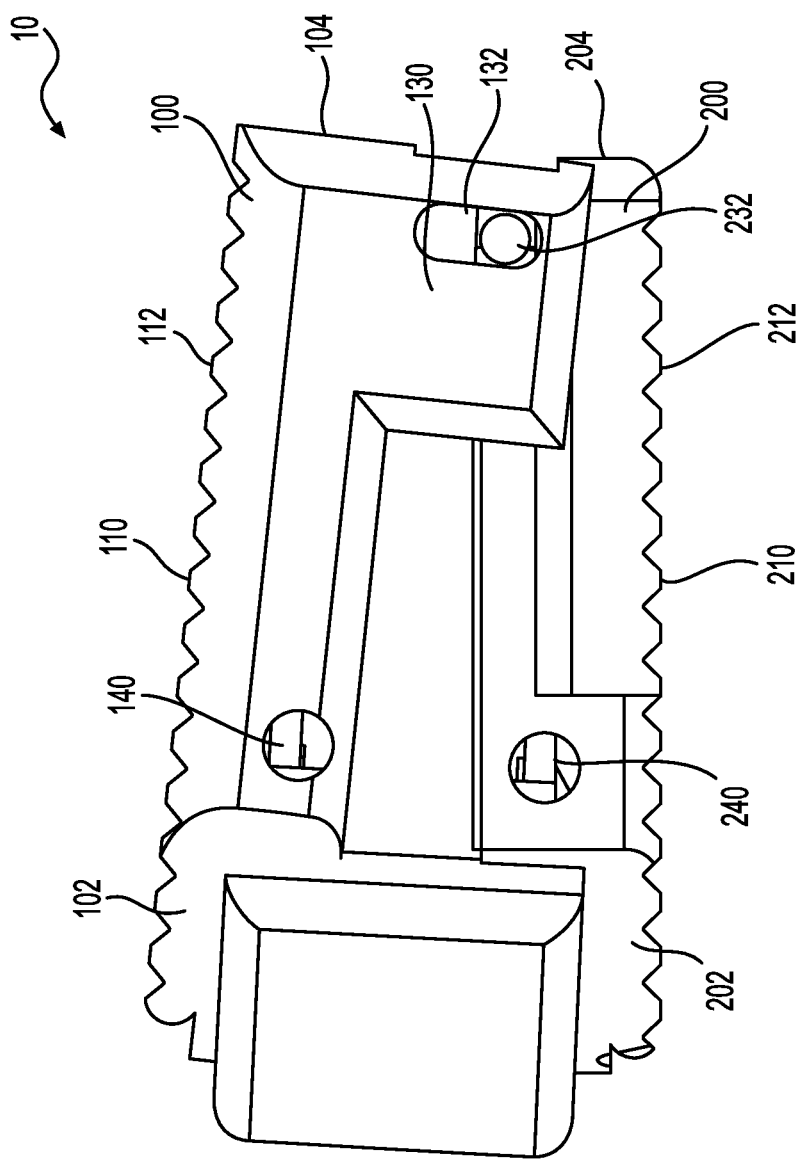
FIG. 2 is a side elevational view of the expandable inter-body fusion device of FIG. 1.
Figure 3:
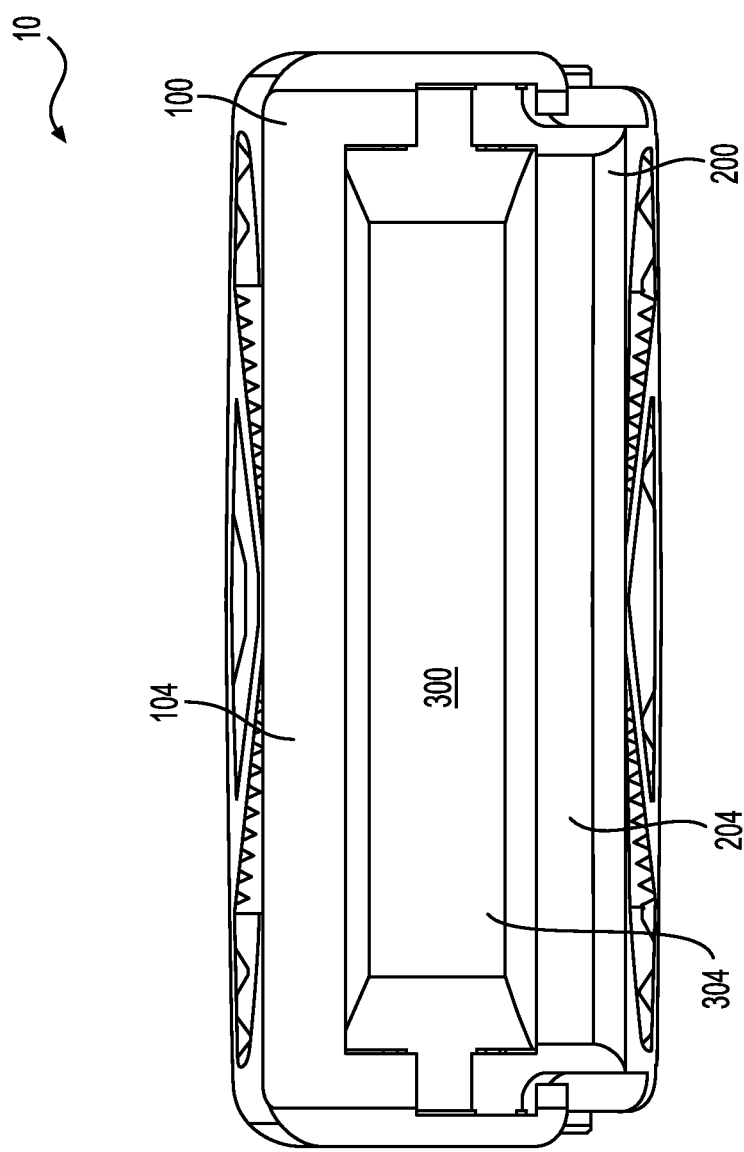
FIG. 3 is a front elevational view of the expandable inter-body fusion device of FIG. 1.
Figure 4:
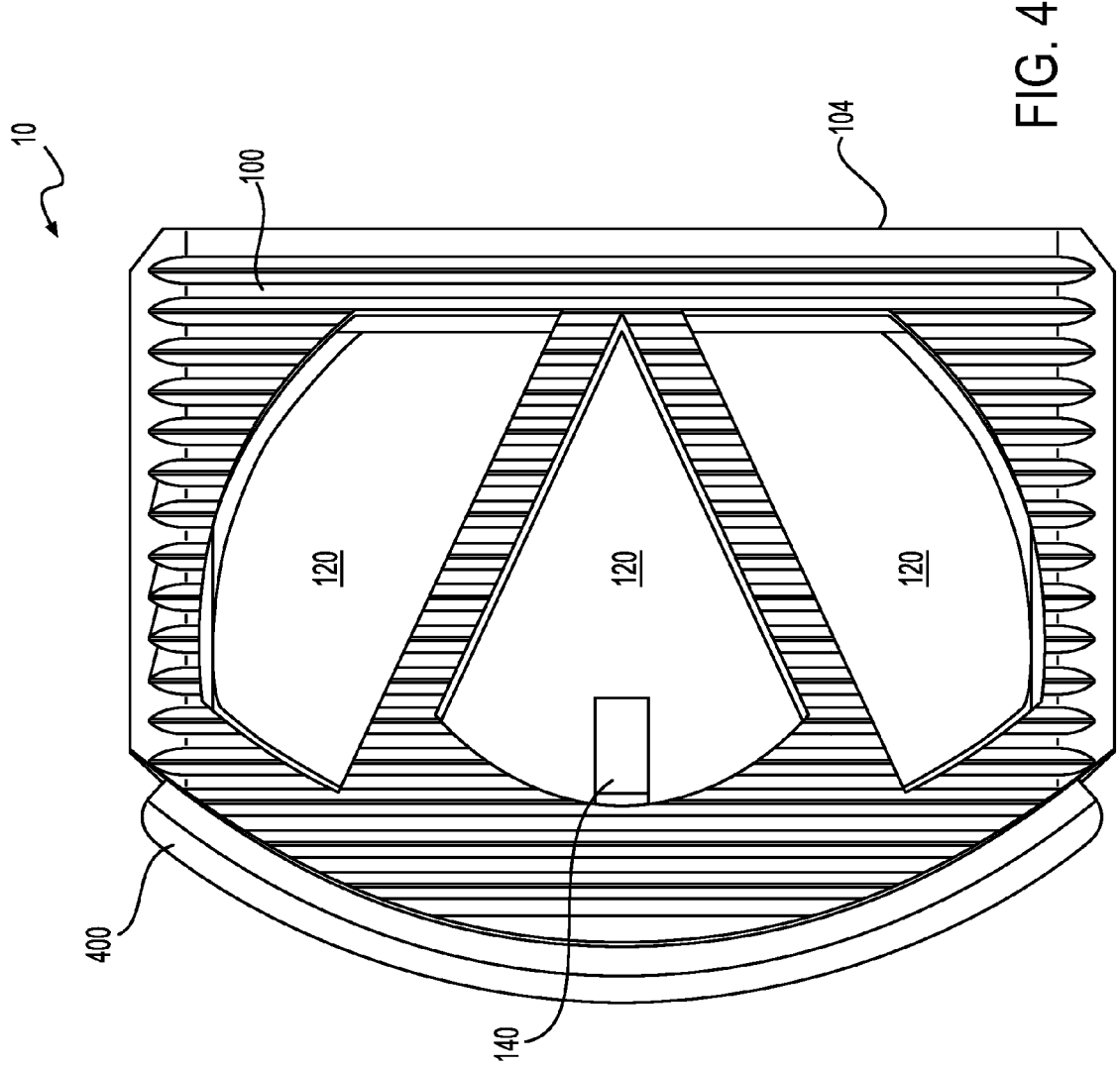
FIG. 4 is a top plan view of the expandable inter-body fusion device of FIG. 1.
Figure 5:
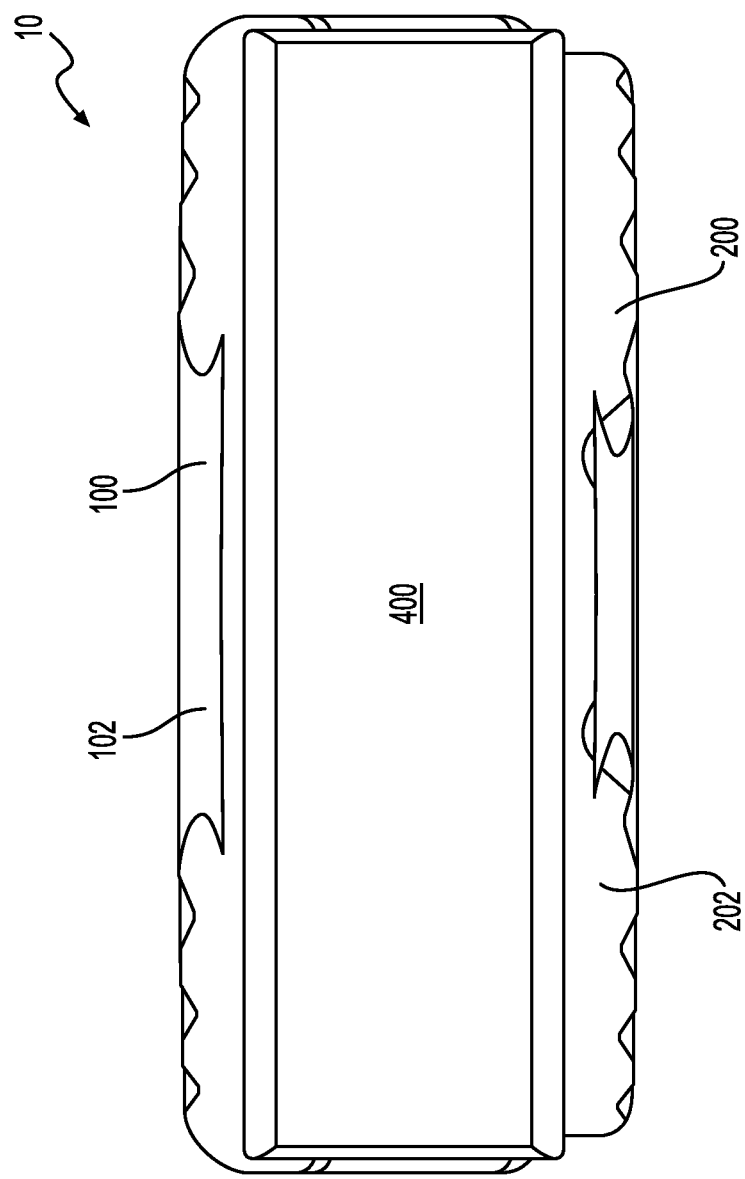
FIG. 5 is a rear elevational view of the expandable inter-body fusion device of FIG. 1.
Figure 6:
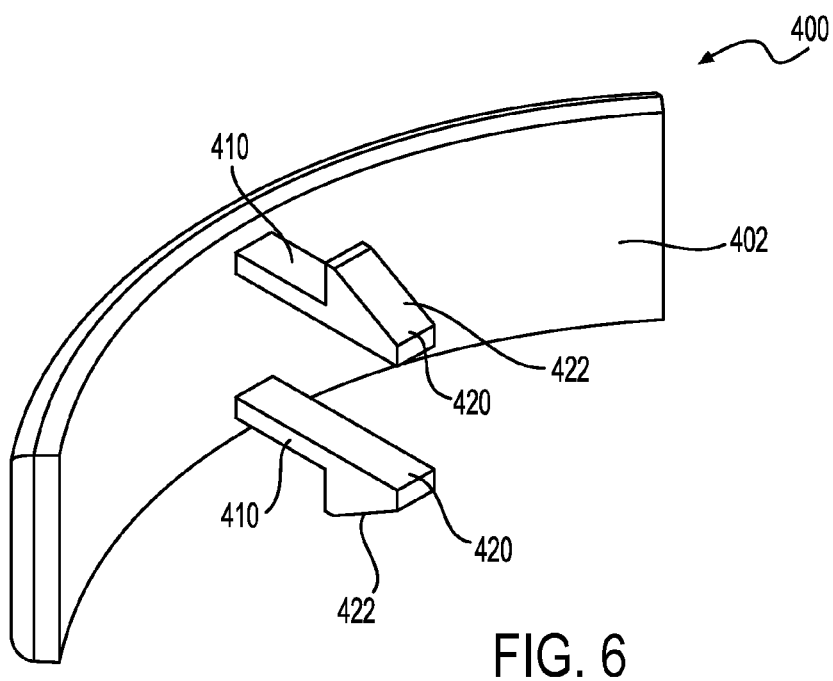
FIG. 6 is a perspective view of an end cap of the expandable inter-body fusion device of FIG. 1.
Figure 7:
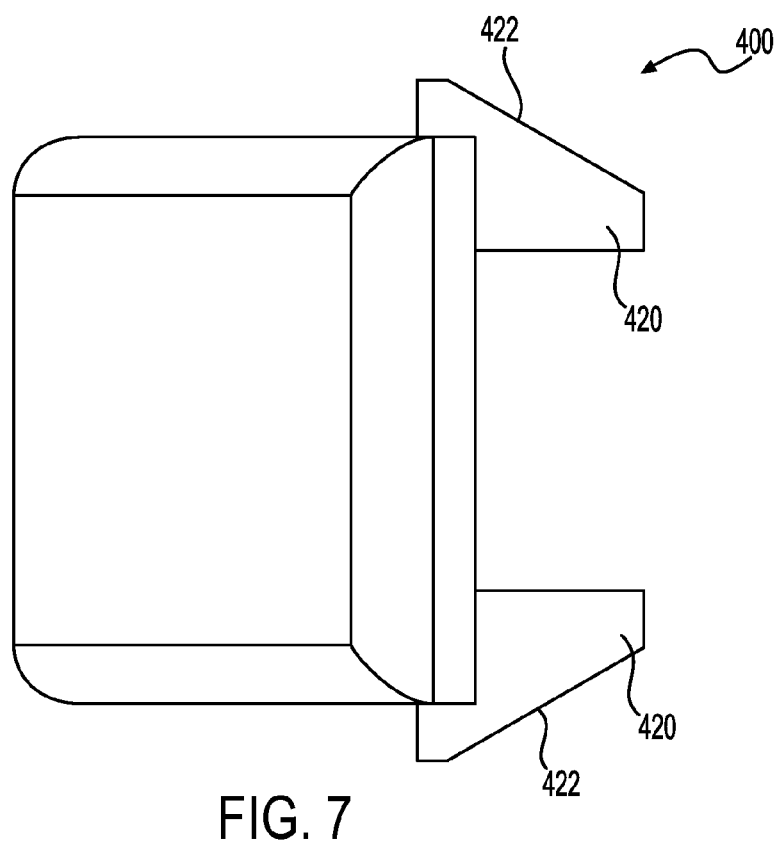
FIG. 7 is a side elevational view of the end cap of FIG. 6.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

In one aspect, presented herein is an expandable inter-body fusion device 10 for use in spinal surgery, such as, but not limited to, ALIF and PLIF procedures. In one aspect, the expandable inter-body fusion device comprises a first plate 100 and a second plate 200. The first plate 100 has an upper bone contact surface 110, a trailing end 102, and a leading end 104. The second plate 200 has a lower bone contact surface 210, a trailing end 202 and a leading end 204.

To assemble the expandable inter-body fusion device 10, in one aspect, the first plate 100 and the second plate 200 can be connected to each other, either directly or indirectly, at or near their leading ends 104, 204. When connected, the first plate 100 and the second plate 200 can be positioned substantially one on top of another, defining an interior cavity 12 therebetween. That is, when the first plate and the second plate are connected or coupled together, at least a portion of the second plate 200 can substantially underlie the first plate 100. In one aspect, the two plates can be connected hingedly in a manner to permit changing the angular relationship between the upper bone contact surface 110 and the lower bone contact surface 210. In another aspect, the two plates can be connected to permit translation of the pivot point of the hinged connection to enable changing of the spatial relationship of the first plate relative to the second plate. In yet another aspect, the first plate 100 and the second plate 200 can be coupled together such that the first plate can both translate and rotate relative to the second plate.

As a result of the connection formed between the first plate 100 and the second plate 200, the cavity volume can be variable. In one aspect, the first plate can be positioned substantially adjacent the second plate in a first position. In the first position, the interior cavity can have a first volume and a first cavity height. Similarly, in the first position, a first angle can be formed between the upper bone contact surface 110 and the lower bone contact surface 210. In another aspect, the first plate 100 can be positioned in a second position relative to the second plate 200 in which at least a portion of the first plate is spaced from the second plate. For example, at least a portion of the first plate 100 can be rotated and/or translated away from the second plate 200. In the second position, the interior cavity 12 can have a second volume that is greater than the first volume, and/or a second cavity height that is greater than the first cavity height. Similarly, in the second position, a second angle can be formed between the upper bone contact surface 110 and the lower bone contact surface 210 that is greater than the first angle.

As can be appreciated, the first angle can be about 0 degrees, such that the first plate 100 and the second plate 200 are substantially parallel to each other. Optionally, the first angle can be about 1 degree, about 2 degrees, about 3 degrees, about 4 degrees, about 5 degrees, about 6 degrees, about 7 degrees, about 8 degrees, about 9 degrees, about 10 degrees, about 15 degrees, about 20 degrees, about 25 degrees, about 30 degrees, about 35 degrees, about 40 degrees, about 45 degrees, and greater than about 45 degrees. As discussed above, the second angle can be greater than the first angle. Optionally, the second angle can be about 1 degree, about 2 degrees, about 3 degrees, about 4 degrees, about 5 degrees, about 6 degrees, about 7 degrees, about 8 degrees, about 9 degrees, about 10 degrees, about 15 degrees, about 20 degrees, about 25 degrees, about 30 degrees, about 35 degrees, about 40 degrees, about 45 degrees, and greater than about 45 degrees.

In an exemplified aspect, at least one of the first plate 100 and the second plate 200 can define at least one graft window 120, 220 that is in communication with the interior cavity 12 defined by the first and second plates. In another aspect, the upper bone contact surface 110 of the first plate comprises a plurality of ridges 112 for frictionally engaging a first vertebra. As can be appreciated, the lower bone contact surface 210 of the second plate can also comprise a plurality of ridges 212 to frictionally engage a second vertebra. In a further aspect, the at least one graft window 120 defined in the first plate 100 can at least partially overlie the at least one graft window 220 of the second plate, thereby permitting bone growth therethrough.

Figure 8:
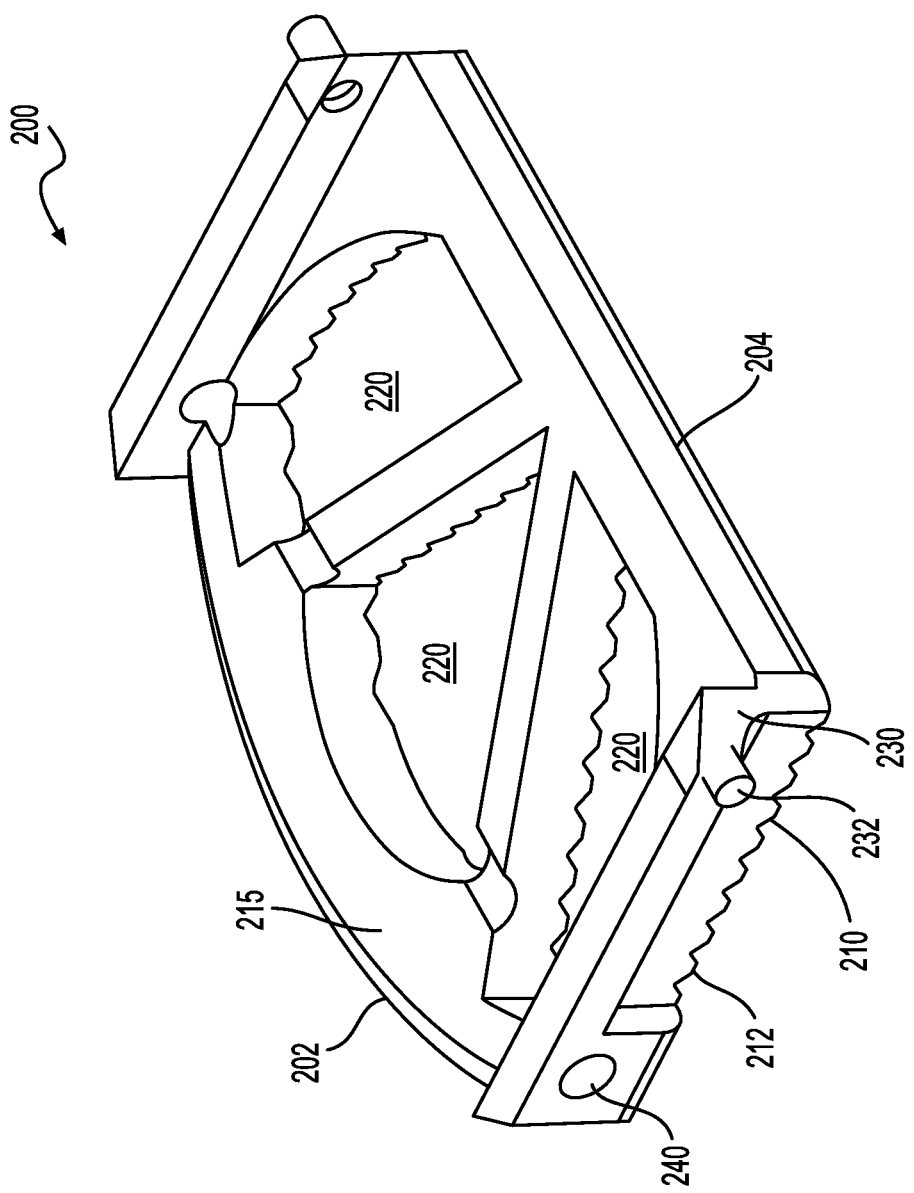
FIG. 8 is a perspective view of the second plate of the expandable inter-body fusion device of FIG. 1.
Figure 9:
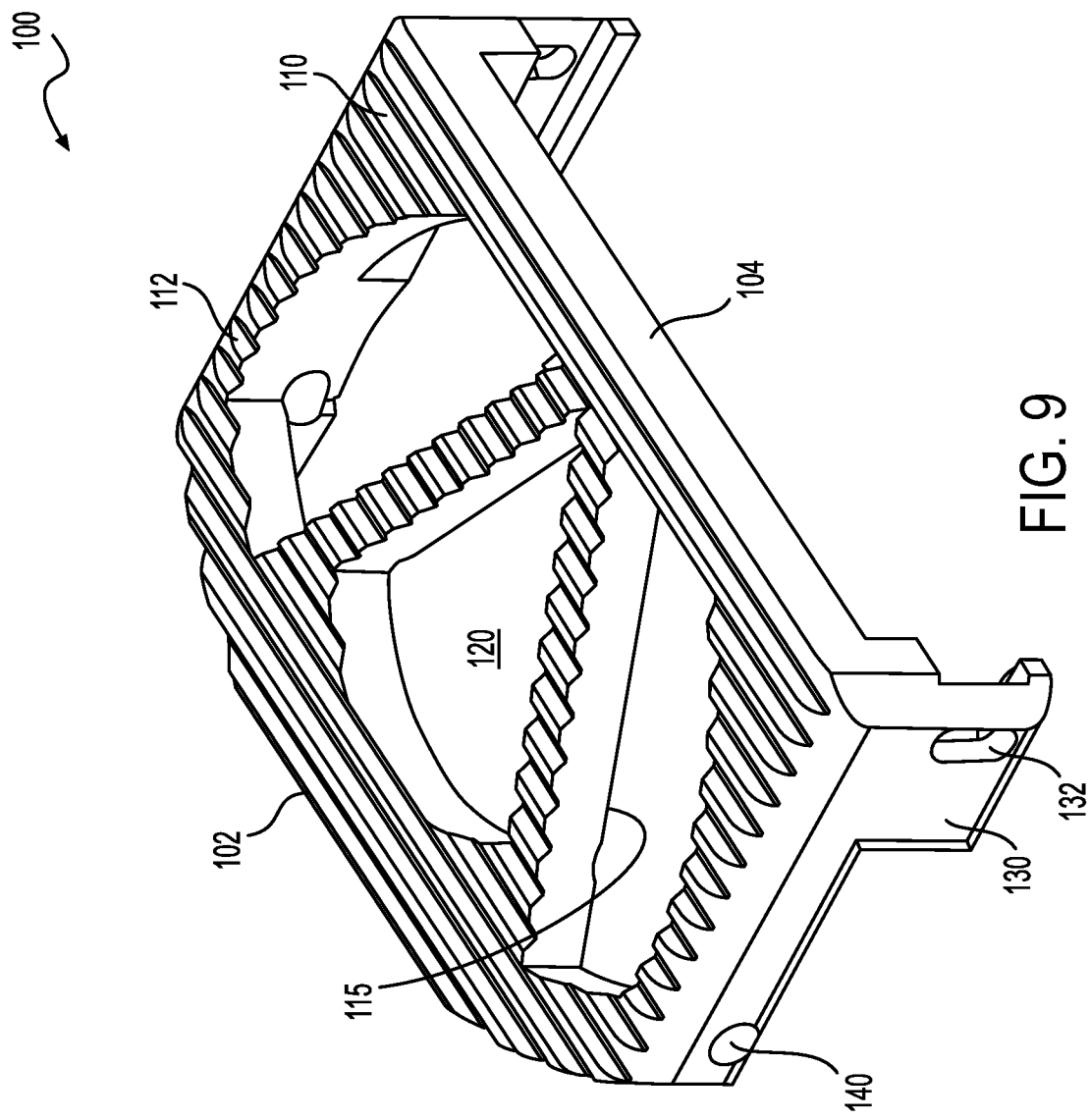
FIG. 9 is a perspective view of the first plate of the expandable inter-body fusion device of FIG. 1.

As shown in FIG. 9, the first plate 100 can comprise a pair of opposed flanges 130 extending down from each side at or near the leading end 104 of the first plate substantially parallel to a longitudinal axis of the first plate. Additionally and with reference to FIG. 8, the second plate 200 can comprise a pair of complimentary flanges 230 extending up from each side at or near the leading end 204 of the second plate substantially parallel to a longitudinal axis of the second plate. When the first plate 100 is positioned over the second plate 200, the respective flanges from each plate can remain substantially adjacent one another. In one aspect, the pair of flanges 230 of the second plate 200 each comprise a male protrusion 232 and the pair of flanges 130 of the first plate each define a slot, elongate recess, or elongate bore 132. As such, the male protrusions of the second plate can complimentarily engage with the slot, recess, or bore of the first plate to connect or couple the second plate 200 to the first plate 100. Upon engagement of the male protrusion and the slot, elongate recess, or elongate bore 132, the male protrusion 232 can be selectively moved within the slot, recess, or elongate bore 132. With this configuration, the relationship of the first plate 100 to the second plate 200 can be changed both in distance and in angle with respect to one another. That is, with this configuration, the first plate and/or the second plate can both rotate and translate relative to the other plate. As such, when implanted, the expandable inter-body fusion device 10 can not only change the spacing between the adjacent vertebrae, but can also induce a desired lordotic angle.

In one aspect, the height of the expandable inter-body fusion device 10 and the height of the interior cavity 12 can vary from about 5 mm to about 20 mm. In another aspect, the height of the expandable inter-body fusion device and the height of the interior cavity can vary from about 8 mm to about 16 mm. In yet another aspect, the height of the expandable inter-body fusion device 10 and the height of the interior cavity 12 can vary from about 10 mm to about 14 mm.

In an exemplified aspect, the angle of the upper bone contact surface 110 relative to the lower bone contact surface 210 (the first angle and/or the second angle) can vary from about −10 degrees to about 15 degrees. In another aspect, the first angle and/or the second angle can vary from about −5 degrees to about 10 degrees. In yet another aspect, the first angle and/or the second angle can vary from about 0 degrees to about 8 degrees.

As shown in the figures, at least one of the first plate 100 and the second plate 200 can define at least one tool bore 140, 240 on either side of the respective plate at or adjacent the trailing end 102, 202 of the plate(s). Additionally, the leading end 104 of the first plate and/or the leading end 204 of the second plate can be tapered, as shown, in order to facilitate insertion between the two adjacent vertebrae.

Figure 10:
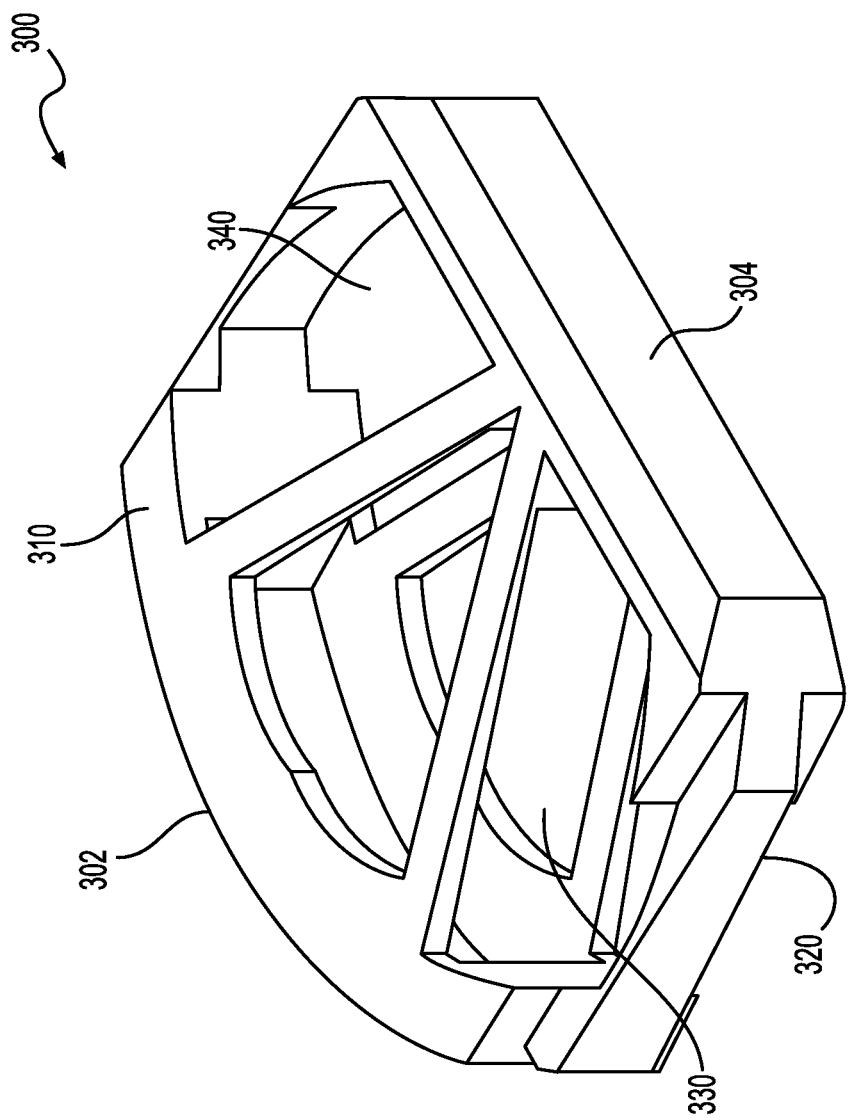
FIG. 10 is a perspective view of the insert of the expandable inter-body fusion device of FIG. 1.
Figure 11:
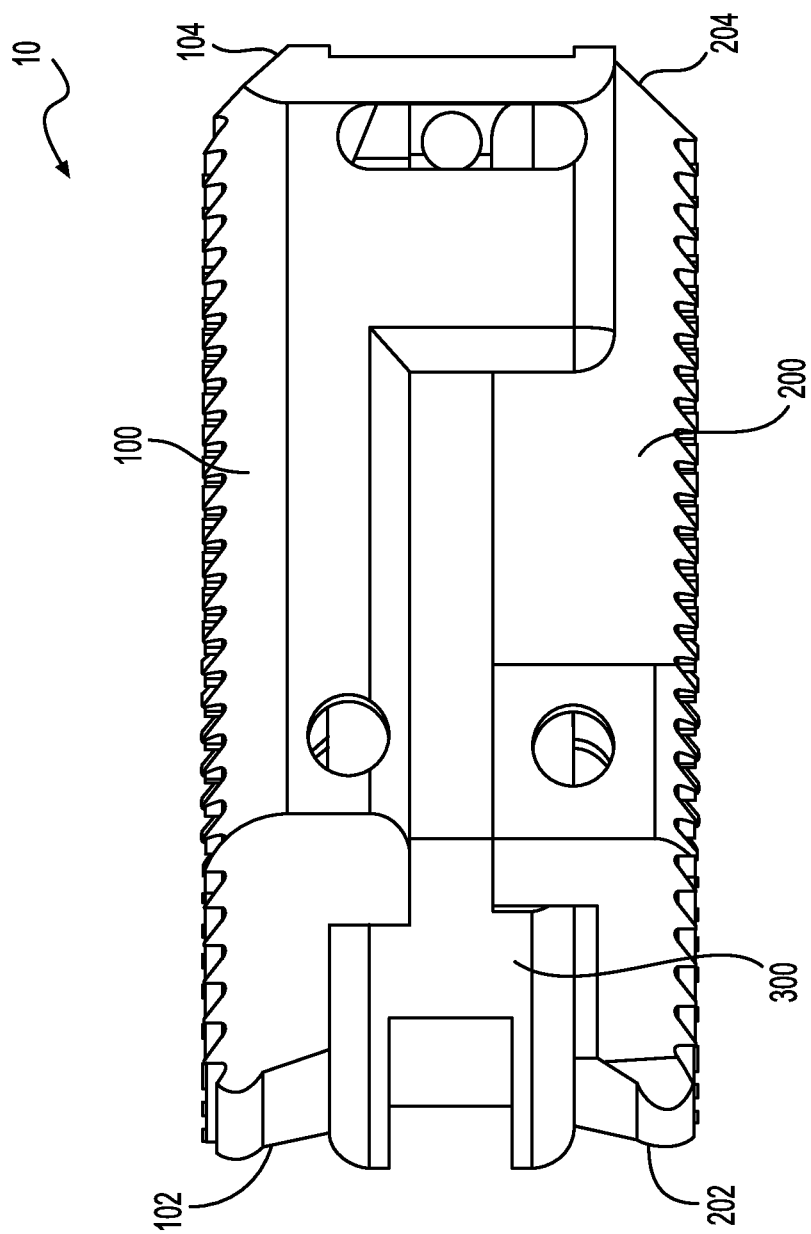
FIG. 11 is a side elevational view of the expandable inter-body fusion device of FIG. 1, showing the expandable inter-body fusion device in first expanded state of height.
Figure 12:
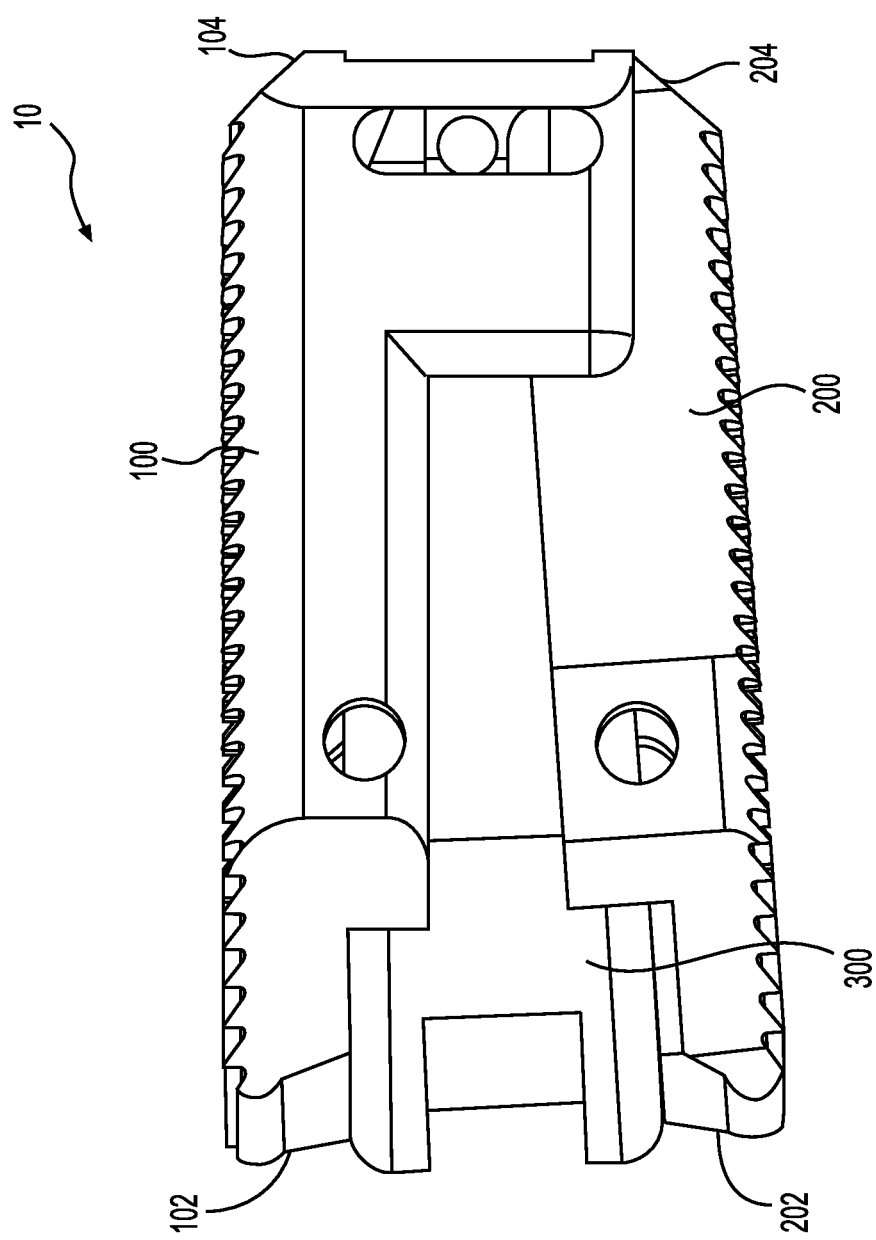
FIG. 12 is a side elevational view of the expandable inter-body fusion device of FIG. 1, showing the expandable inter-body fusion device in second expanded state of height and lordosis.
Figure 13:
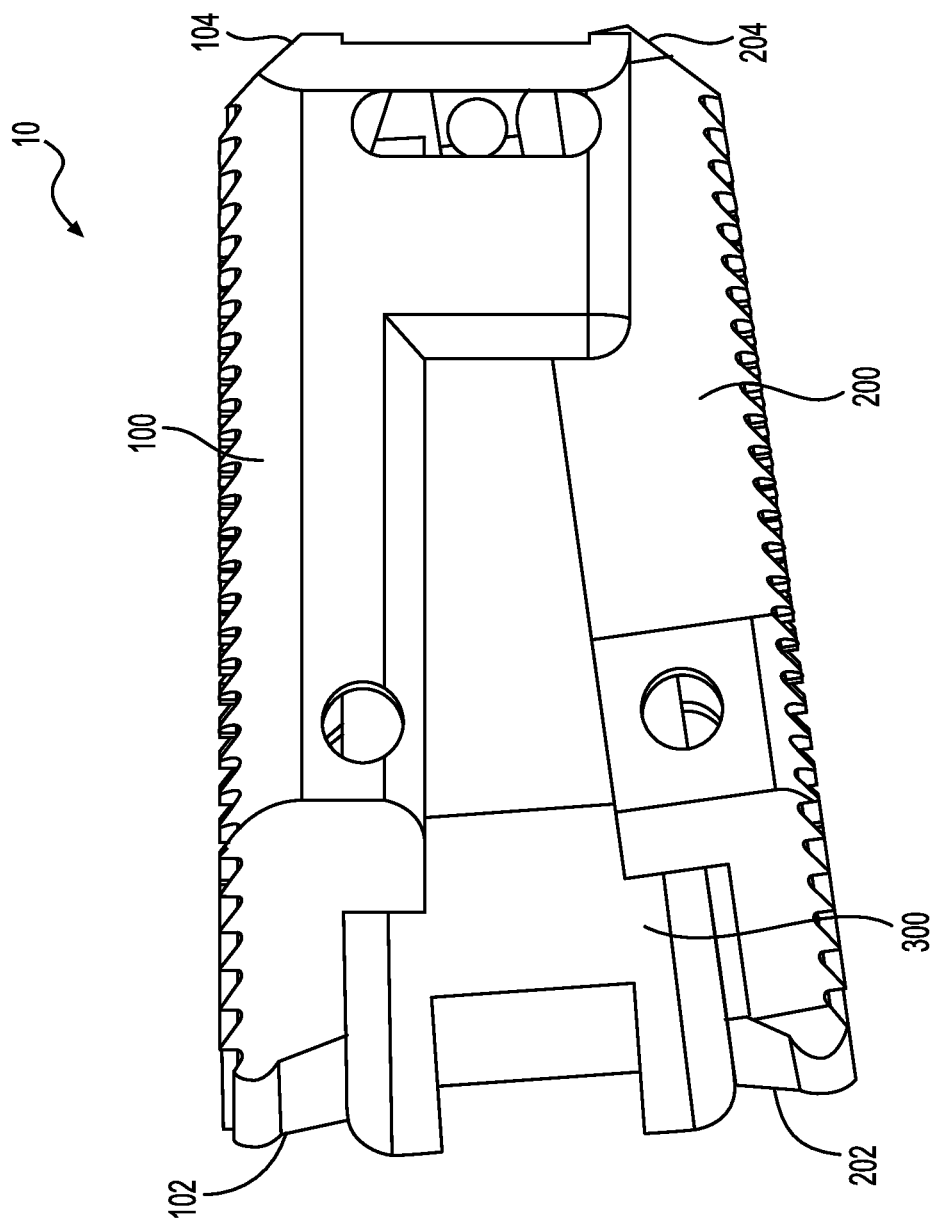
FIG. 13 is a side elevational view of the expandable inter-body fusion device of FIG. 1, showing the expandable inter-body fusion device in third expanded state of height and lordosis.
Figure 14:
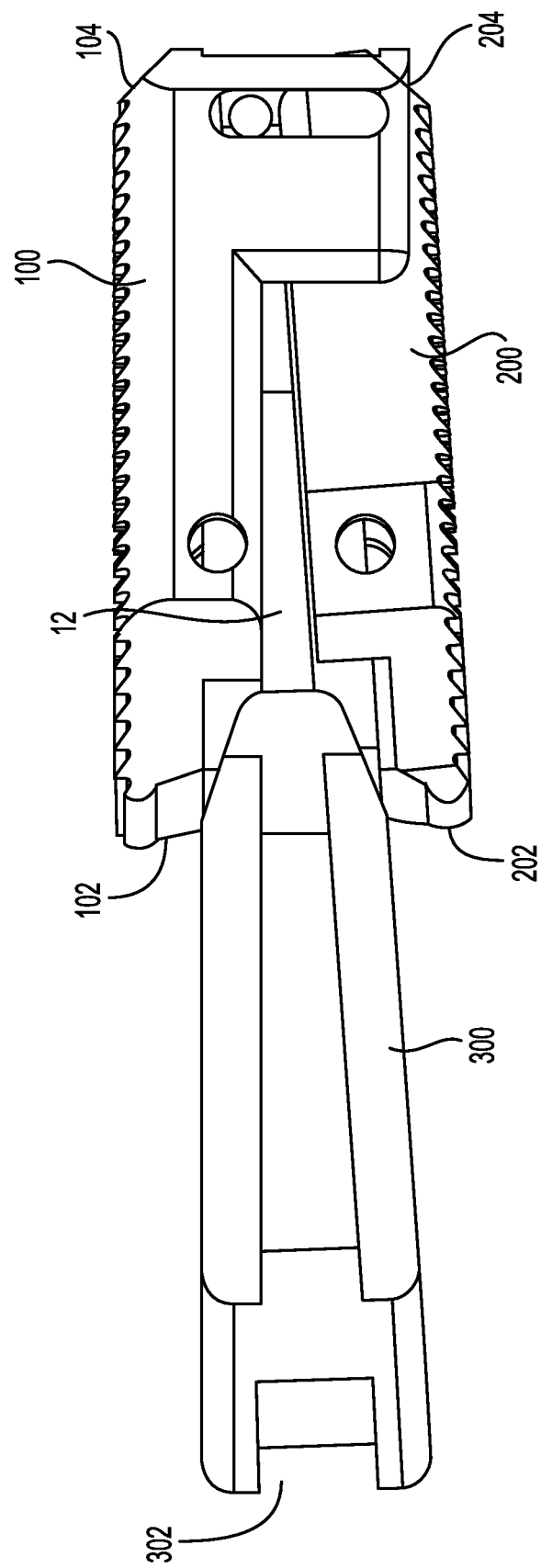
FIG. 14 is a side elevational view of the expandable inter-body fusion device of FIG. 1, showing the insertion of the insert into the interior cavity.

In another aspect, and with reference to FIG. 10, the expandable inter-body fusion device 10 further comprises an insert 300 configured for insertion between the first plate 100 and second plate 200 and substantially into the interior cavity 12. Upon insertion of at least a portion of the insert into the interior cavity, the insert 300 can urge the first plate and/or the second plate to a desired position and orientation relative to each other.

The insert 300 can have a top face 310 configured to engage at least a portion of the first plate 100 and a bottom face 320 configured to engage at least a portion of the second plate 200. A leading edge 304 can be formed between the top face and the bottom face having a leading edge thickness. In one aspect, the top face of the insert 300 can be substantially parallel to the bottom face. Optionally, the top face 310 can be at an angle relative to the bottom face 320. Depending upon the thickness of the leading edge of the insert and/or the angle of the top face relative to the bottom face, the insert 300 can be configured to move either the first or second plate, or both, to substantially set the distance and angle of the upper bone contact surface 110 relative to the lower bone contact surface 210. The leading edge 304 of the insert, in one aspect, can be tapered. In another aspect, the leading edge of the insert 300 can protrude from the leading end 104, 204 of the first plate 100 and the second plate 200 when the insert is inserted into the interior cavity 12.

In one aspect, the insert 300 can define an insert inner cavity 330 and can have a graft window 340 in the top face 310 and/or the bottom face 320 in communication with the insert inner cavity 330. In another aspect, when positioned therein the interior cavity 12 defined by the first plate 100 and the second plate 200, the graft window 340 of the top and/or bottom faces can at least partially overlie the respective graft windows 120, 220 of the first and second plates. In use, the insert inner cavity can be packed with bone fusion material and, when implanted, can promote bone growth through the graft windows of the expandable inter-body fusion device 10. The bone fusion material may comprise, for example and without limitation, autologous bone, allograft bone, bone substitute, osteoinductive agent, and bone cement.

As shown in FIGS. 4-7, the expandable inter-body fusion device 10 can further comprise an end cap 400 configured to engage a portion of the first plate 100 and/or the second plate 200 to enclose at least a portion of the interior cavity 12, according to one aspect. In another aspect, the end cap can be positioned thereon the trailing end 102, 202 of the first plate 100 and/or the second plate 200 of the inter-body fusion device, thereby helping to retain the insert 300 therein the interior cavity 12. In one aspect, the end cap 400 can be shaped to conform to the trailing end 102, 202 of the first and second plates 100, 200. In another aspect, the end cap can be sized to cover and enclose the interior cavity 12 such that the bone fusion material is retained therein. As such, the size of the end cap can be chosen after selection and/or insertion of the insert 300, so that the height of the inter-body fusion device is known.

In one aspect, the end cap 400 comprises at least one tab 410 protruding away from a portion of a front face 402 of the end cap. In another aspect, the tab can be configured to engage a portion of the first plate 100 and/or the second plate 200 to hold the end cap substantially in place. In one aspect, the tab has a head 420 with a cam surface 422. In this aspect, upon insertion of the tab into the interior cavity 12, the cam surface cams a portion of the tab 410 away from a lower surface 115 of the first plate 100 and permits bi-directional movement of the end cap along the longitudinal axis of the first plate and the second plate until the head 420 of the tab reaches an edge of the graft window 120 of the first plate and/or an edge of the graft window 220 of the second plate. Upon the tab 410 reaching the edge of a graft window, the head 420 biases back into substantially its original position and engages the edge of the graft window, thereby retaining the end cap 400 into position against the trailing ends 102, 202 of the first and second plates. It is contemplated that the tab 410 may be configured to engage a portion of the second plate 200, or there may be at least two tabs, where at least one tab could be configured to engage the first plate 100 and at least one tab could be configured to engage the second plate. It is also contemplated that the respective first or second plate can define a recess to retain the head 420 of the tab 410 in lieu of the configuration whereby the head of the tab engaging an edge of a graft window.

Figure 15:
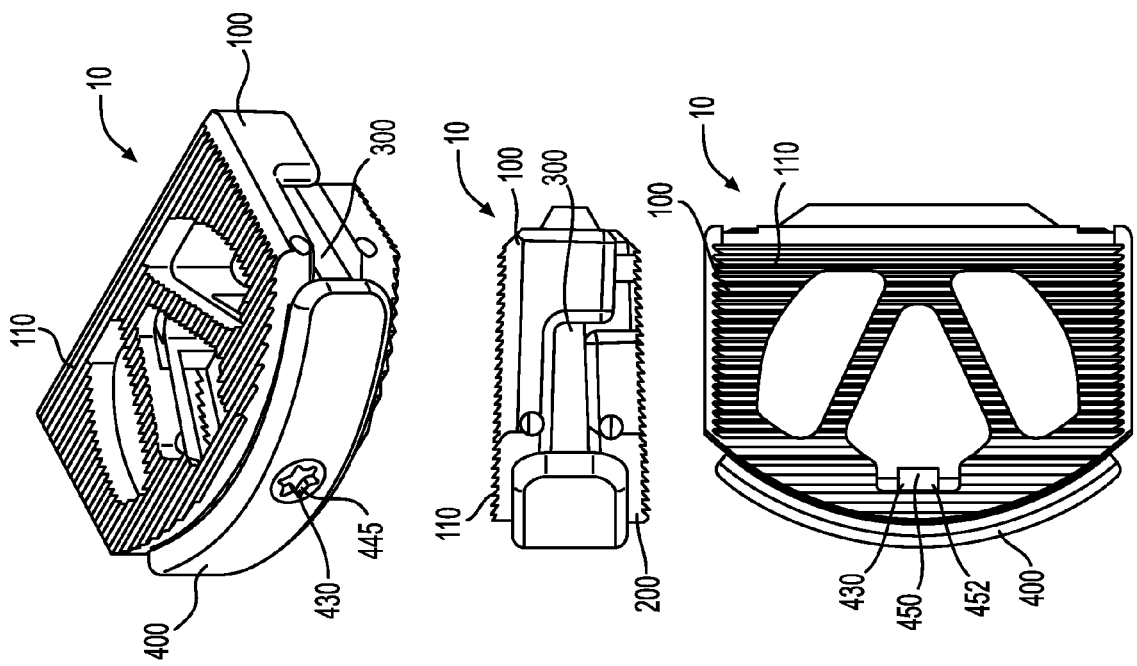
FIG. 15 is a series of various views of the expandable inter-body fusion device of FIG. 1, showing an end cap with a rotationally actuated locking mechanism with flanged blades.
Figure 15:
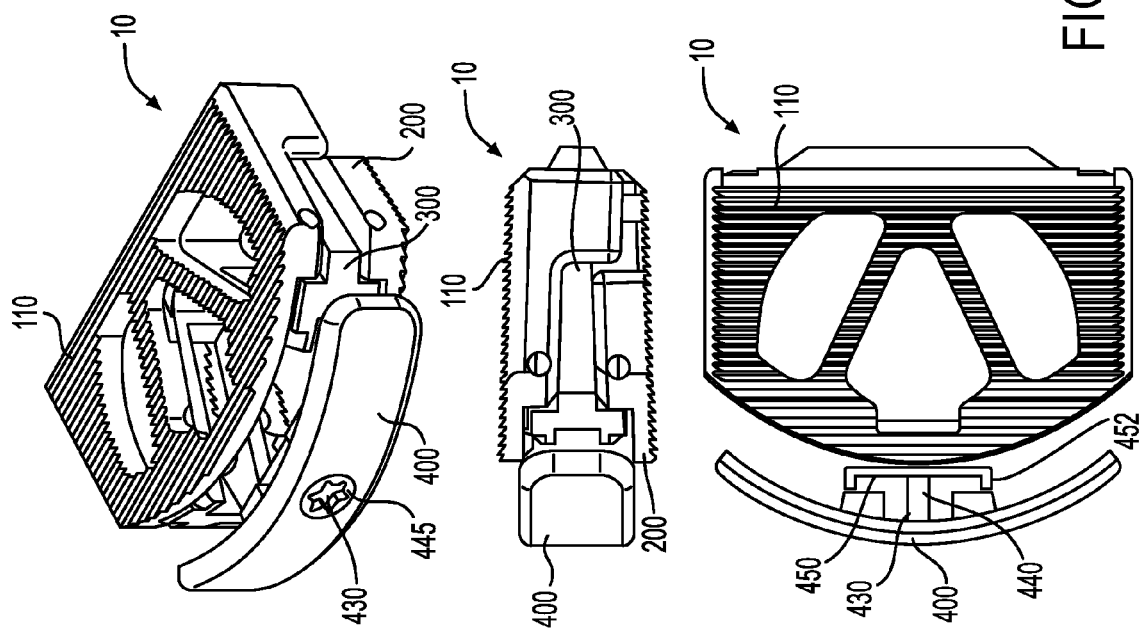

In one aspect, the end cap 400 can comprise a rotationally actuated locking mechanism 430. Although various aspects and embodiments are contemplated, in one aspect, as depicted in FIG. 15, the rotationally actuated locking mechanism comprises a rotatable shaft 440 and a flanged blade 450 positioned on the shaft and substantially transverse to a longitudinal axis of the shaft. In another aspect, a flange 452 can be positioned near or adjacent to each end of the flanged blade. In still another aspect, a locking aperture is defined therethrough the end cap configured to accept the shaft 440 of the locking mechanism. The locking mechanism 430 has a head 445 keyed to accept an insertion tool and sized large enough to be retained in and not pass through the locking aperture. In use, the end cap can be inserted into the interior cavity 12 with the flanged blade 450 in a first blade position substantially parallel to a plane containing the longitudinal axis of the end cap. Once positioned, the shaft 440 can be rotated to a second blade position, resulting in the rotation of the flanged blade into a position substantially perpendicular to the plane containing the longitudinal axis of the end cap 400. Upon rotation of the shaft towards the second blade position, at a predetermined angle, a portion of the flanged blade can engage the first plate 100 and/or the second plate 200. At least one flange 452 of the flanged blade 450 can be configured to engage and lock into portions of the first and/or second plates.

Figure 16:
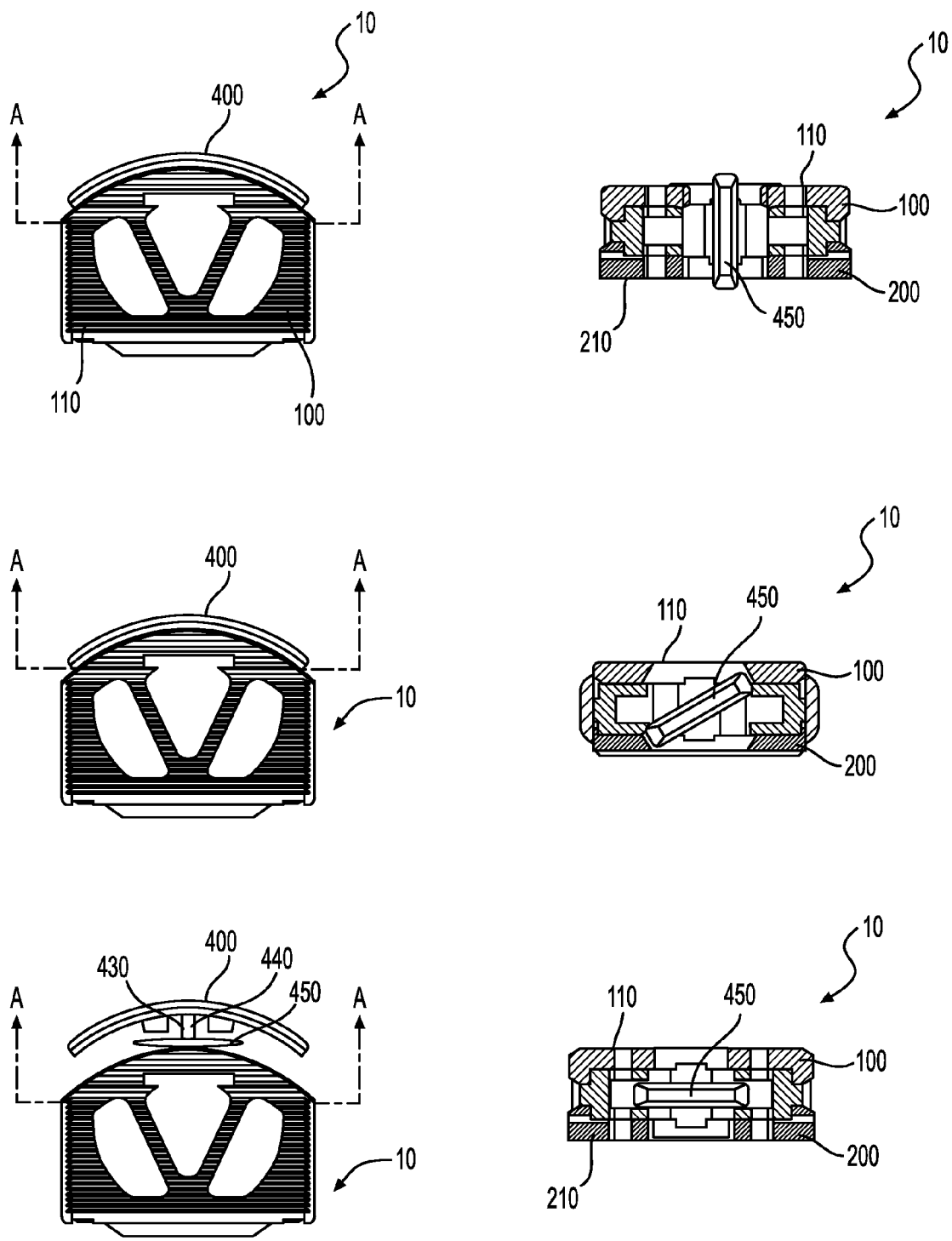
FIG. 16 is a series of various views of the expandable inter-body fusion device of FIG. 1, showing an end cap with a rotationally actuated locking mechanism with bone-engaging blades.

In still another aspect, as shown in FIG. 16, the flanged blade 450 can be long enough so that when the end cap 400 is inserted into the interior cavity 12 and rotated to the second blade position, at least a portion of the flanged blade extends past the upper bone contact surface 110 and/or the lower bone contact surface 210 and into the bony structure of adjacent vertebrae. In this aspect, the blade can comprise sufficiently sharp edges.

Figure 17:
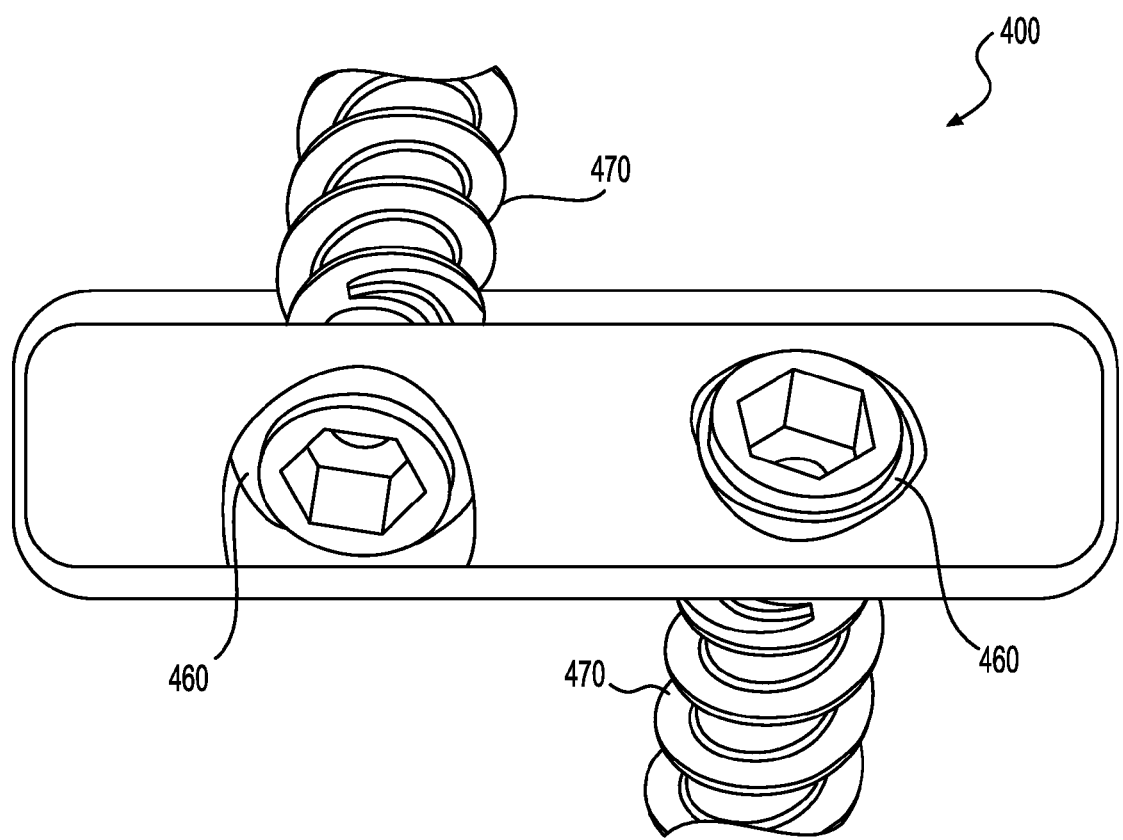
FIG. 17 is one aspect of an end cap for use with the expandable inter-body fusion device of FIG. 1, showing an end cap defining a pair of screw apertures.

Referring now to FIG. 17, the end cap 400 can further comprise one or more screw apertures 460 configured for receipt of one or more bone screws 470. The bone screws, as illustrated, can be angled to be driven up or down through the end cap and into the adjacent vertebrae. The bone screws can comprise retention mechanisms known in the art, as well.

Also presented herein is a method of using an expandable inter-body fusion device 10 during an inter-body fusion procedure. In one aspect, the method comprises accessing the desired disc space, choosing the correct size of insert 300 with the appropriate height and angle, inserting the first plate 100 and the second plate 200 into the disc space, inserting the insert into the interior cavity 12, and placing the end cap 400 into position on at least one of the trailing end 102, 202 of the first and second plates. An additional step of packing the insert with bone fusion material prior to insertion is also contemplated.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An expandable inter-body fusion device for use in spinal surgery, comprising;
    a first plate having an upper bone contact surface, a first end, and a second end; and
    a second plate having a lower bone contact surface, a first end, and a second end, the second plate substantially underlying the first plate and, together, the first and second plates defining an interior cavity having a cavity height and a cavity volume therebetween, wherein one of the first plate and the second plate defines a plurality of substantially vertically disposed slots substantially adjacent the second end, and the other of the first plate and the second plate comprises a corresponding plurality of male protrusions substantially adjacent the second end and disposed therein the slots, creating a sliding pivot point, and wherein the interior cavity is configured to receive an insert in a direction from the first end to the second end, and wherein insertion of the insert into the interior cavity selectively and independently increases the cavity height and an angle formed by the first and second plates.

2. The device of claim 1, wherein in a first position, the interior cavity has a first height, and in a second position, the interior cavity has a second height that is greater than the first height.

3. The device of claim 2, wherein in the first position, a first angle is formed between the upper bone contact surface and the lower bone contact surface, and in the second position, a second angle is formed between the upper bone contact surface and the lower bone contact surface that is greater than the first angle.

4. The device of claim 3, wherein at least one of the first angle and the second angle is a lordotic angle.

5. The device of claim 3, wherein the first ends of the first and second plates are the leading ends.

6. The device of claim 3, further comprising an insert having a top face, a bottom face, and a leading edge having a leading edge thickness, wherein the top face is at a third angle relative to the bottom face, and wherein at least a portion of the insert is configured to be inserted into the interior cavity.

7. The device of claim 6, wherein upon insertion of at least a portion of the insert into the interior cavity, the top face engages a portion of the first plate and the bottom face engages a portion of the second plate.

8. The device of claim 7, wherein, the insert is configured to set at least one of the second cavity height and the second angle depending upon the leading edge thickness and the third angle.

9. The device of claim 8, wherein an insert inner cavity is defined therein the insert, and wherein the insert inner cavity is configured to be packed with a bone fusion material.

10. The device of claim 6, further comprising an end cap configured to engage a portion of at least one of the first plate and the second plate to retain the insert therein the interior cavity.

11. The device of claim 1, further comprising an end cap configured to engage a portion of at least one of the first plate and the second plate to enclose at least a portion of the interior cavity.

12. The device of claim 11, wherein the end cap comprises at least one tab protruding away from a portion of a front face of the end cap, and wherein the at least one tab is configured to engage a portion of at least of the first plate and the second plate to hold the end cap substantially in place.

13. The device of claim 11, wherein the end cap comprises a rotationally actuated locking mechanism.

14. The device of claim 13, wherein the rotationally actuated locking mechanism comprises a rotatable shaft and a flanged blade positioned on the shaft substantially transverse to a longitudinal axis of the shaft.

15. The device of claim 14, wherein the flanged blade of the end cap is rotatable about and between a first blade position, in which the flanged blade is substantially parallel to a plane containing the longitudinal axis of the end cap and a second blade position, in which the flanged blade is substantially perpendicular to the plane containing the longitudinal axis of the end cap.

16. The device of claim 15, wherein in the second blade position, at least a portion of the flanged blade is configured to engage at least one of the first and second plates.

17. The device of claim 15, wherein in the second blade position, at least a portion of the flanged blade is configured to engage adjacent bony structure.

18. An expandable inter-body fusion device for use in spinal surgery, comprising;
    a first plate having an upper bone contact surface, a leading end, and a trailing end;
    a second plate having a lower bone contact surface, a first end, and a second end, the second plate substantially underlying the first plate and, together, the first and second plates defining an interior cavity, wherein the second plate has a lower bone contact surface, a leading end, and a trailing end, wherein the second plate is hingedly connected to a portion of the first plate adjacent the leading end of the first and second plates, wherein one of the first plate and the second plate defines a plurality of substantially vertically disposed slots and the other of the first plate and the second plate comprises a corresponding plurality of male protrusions disposed therein the slots, creating a sliding pivot point
    an insert having a top face, a bottom face, a leading edge having a leading edge thickness, and a relative angle of the top face with respect to the bottom face, wherein when at least a portion of the insert is positioned therein the interior cavity, the top face engages a portion of the first plate and the bottom face engages a portion of the second plate, and wherein the insert is configured to be received into the interior cavity in a direction from the trailing end to the leading end and to set at least one of the cavity height and the angle of the upper contact surface relative to the lower contact surface when the insert is positioned therein the interior cavity, and wherein the cavity height adjacent the leading end can be set independently of the angle of the upper contact surface relative to the lower contact surface.

19. The device of claim 18, wherein the insert is configured to set at least one of the cavity height and the angle of the upper contact surface relative to the lower contact surface depending upon at least one of the leading edge thickness and the relative angle of the top face with respect to the bottom face.

20. The device of claim 19, wherein the first and the second plates are configured to move about and between a first position, in which the first plate is substantially adjacent the second plate and the interior cavity has a first volume, and a second position, in which at least a portion of the first plate is spaced from the second plate and the interior cavity has a second volume that is greater than the first volume.

21. The device of claim 20, wherein in the first position, the interior cavity has a first height, and in the second position, the interior cavity has a second height that is greater than the first height.

22. The device of claim 21, wherein in the first position, a first angle is formed between the upper bone contact surface and the lower bone contact surface and in the second position, a second angle is formed between the upper bone contact surface and the lower bone contact surface that is greater than the first angle.

23. The device of claim 22, further comprising an end cap configured to engage a portion of at least one of the first plate and the second plate to retain the insert therein the interior cavity.

24. The device of claim 23, wherein the end cap comprises at least one screw aperture configured for receipt of at least one bone screw.

* * * * *